(12) United States Patent
Newton et al.

(10) Patent No.: US 7,981,117 B2
(45) Date of Patent: Jul. 19, 2011

(54) SCREW PLACEMENT GUIDE

(75) Inventors: Peter Newton, San Diego, CA (US); Mark Gracia, Rochester, MA (US); Michael S. Varieur, Portsmouth, RI (US); Carrie A. Breech, Wrentham, MA (US)

(73) Assignee: DePuy Spine, Inc., Raynham, MA (US)

( * ) Notice: Subject to any disclaimer, the term of this patent is extended or adjusted under 35 U.S.C. 154(b) by 726 days.

(21) Appl. No.: 11/946,382

(22) Filed: Nov. 28, 2007

(65) Prior Publication Data
US 2008/0071285 A1 Mar. 20, 2008

Related U.S. Application Data

(62) Division of application No. 10/256,636, filed on Sep. 27, 2002, now abandoned.

(60) Provisional application No. 60/400,912, filed on Aug. 2, 2002.

(51) Int. Cl.
*A61B 17/58* (2006.01)
*A61F 2/00* (2006.01)

(52) U.S. Cl. ........................................................ 606/104

(58) Field of Classification Search ............... 606/86 R, 606/99, 104
See application file for complete search history.

(56) References Cited

U.S. PATENT DOCUMENTS

| | | | |
|---|---|---|---|
| 4,409,968 A * | 10/1983 | Drummond | 606/86 A |
| 5,102,412 A | 4/1992 | Rogozinski | |
| 5,474,558 A | 12/1995 | Neubardt | |
| 5,593,407 A | 1/1997 | Reis | |
| 5,797,918 A | 8/1998 | McGuire et al. | |
| 6,033,406 A | 3/2000 | Mathews | |
| 6,139,551 A | 10/2000 | Michelson et al. | |
| 6,162,170 A | 12/2000 | Foley et al. | |
| 6,306,139 B1 | 10/2001 | Fuentes | |
| 6,342,056 B1 | 1/2002 | Mac-Thiong et al. | |
| 6,436,100 B1 | 8/2002 | Berger | |
| 6,669,698 B1 * | 12/2003 | Tromanhauser et al. | 606/86 A |
| 2002/0082598 A1 | 6/2002 | Teitelbaum | |

FOREIGN PATENT DOCUMENTS

| | | |
|---|---|---|
| EP | 0 995 403 A1 | 4/2000 |
| EP | 1 284 122 A2 | 2/2003 |
| WO | WO 02/45591 A2 | 6/2002 |

OTHER PUBLICATIONS

International Search Report, issued in corresponding PCT/US03/23805, mailed Dec. 3, 2003.

* cited by examiner

*Primary Examiner* — Anu Ramana
(74) *Attorney, Agent, or Firm* — Nutter McClellen & Fish LLP

(57) ABSTRACT

A screw placement guide tool for use in minimally invasive surgery has a proximal handle portion, an extension member extending distally from the handle portion, and an alignment element connected transversely to a distal portion of the extension member and having a screw placement guide located thereon. In this aspect of the invention, the tool is configured so that a surgeon may operate the tool using the handle portion external to a patient's body to align the alignment element with implanted screws so that the screw placement guide indicates a desired position for implantation of an additional screw. Systems and methods for placing a rod receiving screw are also provided.

31 Claims, 4 Drawing Sheets

SCREW PLACEMENT GUIDE

RELATED APPLICATIONS

This application is a divisional application of U.S. patent application Ser. No. 10/256,636, filed on Sep. 27, 2002 and entitled "Screw Placement Guide," and this application further claims priority to provisional application U.S. Ser. No. 60/400,912, filed Aug. 2, 2002, each of which are expressly incorporated by reference herein.

FIELD OF THE INVENTION

The present invention relates to devices and methods for placing a screw to be inserted in a patient's vertebrae during spinal fixation surgery.

BACKGROUND OF THE INVENTION

The use of spinal fixation instrumentation to align and/or fix a desired relationship between adjacent vertebral bodies is well established. Such instrumentation typically includes a spinal fixation element, such as a relatively rigid fixation rod, that is coupled to adjacent vertebrae by attaching the element to screws which have been inserted into the patient's vertebrae or to spinal hooks which can be placed into a vertebral arch for coupling to the vertebral bodies. Once installed, the spinal fixation instrumentation holds the vertebrae in a desired spatial relationship, either until desired healing or spinal fusion has taken place, or for some longer period of time.

One example of a rod based spinal fixation system is provided in U.S. Pat. No. 5,005,562, issued Apr. 9, 1991 to Cotrel (which is hereby incorporated by reference). This system includes pedicle screws and spinal hook vertebral coupling elements (both screws and hooks) having integral U-shaped bodies that extend outward from the vertebrae to which they are attached. A spinal fixation rod is shaped as desired and fitted into the "U" of U-shaped bodies of adjacent vertebrae. The inner surfaces of the U-shaped body are threaded to accept a set screw, and rod is fixed to the vertebral coupling elements by threading a set screw into each of the U-shaped bodies to lock in the rod.

U.S. Pat. No. 5,545,165, issued Aug. 13, 1996 to Biedermann et al. (and incorporated herein by reference), illustrates an improvement in closure systems for fixing a rod to vertebral coupling elements over those provided by Cotrel. The Biedermann et al. system also uses pedicle screws and spinal hooks having U-shaped bodies that extend outward from the vertebrae to which they are attached. The U-shaped bodies of the Biedermann et al. system are threaded on both the inside and the outside. The rod is therefore locked in by both an inner set screw and an outer lock nut. In the illustrated embodiments, the inner set screw is adapted to be driven on its threads using a hex-shaped driver element, and the outer locking nut is provided with hex-shaped flat outer surfaces suitable for engagement with a wrench or similar driving tool.

U.S. Pat. No. 5,443,467, issued Aug. 22, 1995 to Biedermann et al. (and incorporated herein by reference) illustrates the use of an inner set screw and an outer lock nut to lock a rod into a U-shaped body in a polyaxial screw system. In this system, a pedicle screw having a spherical head is captured within a separate U-shaped receiver body. The angle of the screw with respect to the body can be changed until a headlocking element is tightened to lock the angle of the screw head within the receiver body. According to Biedermann et al., this combination of an inner set screw and an outer locking nut provides an advantage in that the force acting on the rod can be independently adjusted by either the inner set screw or the outer locking nut—a particularly useful advantage where the rod being fastened is curved and an exact fastening might only be possible by independent adjustment of the two closure elements. In addition, when tightened, the inner set screw and the outer locking nut tend to lock each other in their tightened positions.

The effectiveness of these spinal fixation systems and others depend upon the rod receiving screws being properly placed. If the rod receiving screws are out of line, the surgeon will be able to place the rod within the receiving portions of the screw assemblies only by placing a load on the screw in order to move it into line to accept the rod. Such loads can result in improper alignment of the vertebrae, premature screw pull out, and fracture of the bone to which the screw is attached.

Accordingly, there is a need for a system, method and/or device to allow the surgeon to place the rod receiving screws in proper alignment before the rod is fitted to them.

SUMMARY OF THE INVENTION

The present invention provides a system, device and method for placing rod receiving screws for implantation in spinal fixation surgery to ensure that rod receiving screws are properly placed so that, as a result of ensuring correct screw placement, surgeons will not need to apply undue force to orient the rod receiving screws to receive the spinal fixation rod to be implanted. The system, device and method of the invention can be advantageously adapted to be particularly useful in minimally invasive surgery. In a first aspect of the invention, a screw placement guide tool for use in minimally invasive surgery is provided having a proximal handle portion, an extension member extending distally from the handle portion, and an alignment element connected transversely to a distal portion of the extension member and having a screw placement guide located thereon. In this aspect of the invention, the tool is configured so that a surgeon may operate the tool using the handle portion external to a patient's body to align the alignment element with implanted screws so that the screw placement guide indicates a desired position for implantation of an additional screw.

In particular embodiments of the invention, the alignment element can be curved to correspond to a curve of a spinal fixation rod to be implanted. The alignment element can also be configured to be elongate with first and second opposed ends and to be connected to the extension member at a first opposed end with the screw placement guide located on the second opposed end. A curved portion can also connect the extension member to the alignment element. In one embodiment, the screw placement guide is a closed loop.

In a further aspect of the invention, a system for placing a rod receiving screw within a patient's bone is provided. The system includes a plurality of rod receiving screws with each rod receiving screw having a proximal rod receiving opening and a distal bone attachment portion, and a screw placement guide tool. The screw placement guide tool has an elongate alignment element including a screw placement guide located thereon. The elongate alignment element is sized to fit within the rod receiving opening of at least one of the plurality of rod receiving screws when the at least one rod receiving screw is implanted and to extend so that the screw placement guide indicates a placement location for another of the plurality of rod receiving screws. In a further embodiment, at least three rod receiving screws are provided and the alignment element is sized to fit within the rod receiving opening of at least two of the at least three rod receiving screws when the at least two rod receiving screws are implanted and to extend so that the screw placement guide indicates a placement location for a third rod receiving screw.

In one embodiment of the invention, the system further includes a marking tool that is guidable to a location indicated by the screw placement guide for placing an indication on a patient's bone where a screw is to be implanted. In further particular embodiments, the screw placement guide tool can include a proximally extending extension member with a handle and the alignment element can be curved to correspond to a curve of a spinal fixation rod to be implanted. The alignment element can also be configured to be elongate with first and second opposed ends and to be connected to the extension member at a first opposed end with the screw placement guide located on the second opposed end.

In a still further aspect of the invention, a method for placing a rod receiving screw for implantation in a vertebral body is provided. In the method, at least one rod receiving screw is implanted into a patient's spine with each screw having a distal bone attachment element and a proximal rod receiving opening. A screw placement guide tool having an elongate alignment element including a screw placement guide located thereon is then fitted within the rod receiving opening of the at least one implanted rod receiving screw so that the screw placement guide indicates a placement location for another receiving screw. In a further embodiment, at least two rod receiving screws are implanted and the alignment element is fitted within the rod receiving opening of the at least two implanted rod receiving screws and to extend so that the screw placement guide indicates a placement location for a third rod receiving screw.

In a further embodiment, a marking tool is also provided and guided to a location indicated by the screw placement guide and an indication is placed on a patient's bone where a screw is to be implanted using the marking tool. In further particular embodiments, the screw placement guide tool can include a proximally extending extension member with a handle and the alignment element can be curved to correspond to a curve of a spinal fixation rod to be implanted. The alignment element can also be configured to be elongate with first and second opposed ends and to be connected to the extension member at a first opposed end with the screw placement guide located on the second opposed end.

BRIEF DESCRIPTION OF THE DRAWINGS

The invention will be more fully understood from the following detailed description taken in conjunction with the accompanying drawings.

DETAILED DESCRIPTION OF THE INVENTION

The present invention provides a system, device and method for placing rod receiving screws for implantation in spinal fixation surgery. The system, device and method of the invention can be configured to be particularly useful in minimally invasive surgery to ensure that rod receiving screws are properly placed so that, as a result of ensuring correct screw placement, surgeons will not need to apply undue force to orient the rod receiving screws to receive the spinal fixation rod to be implanted.

Figure 1:
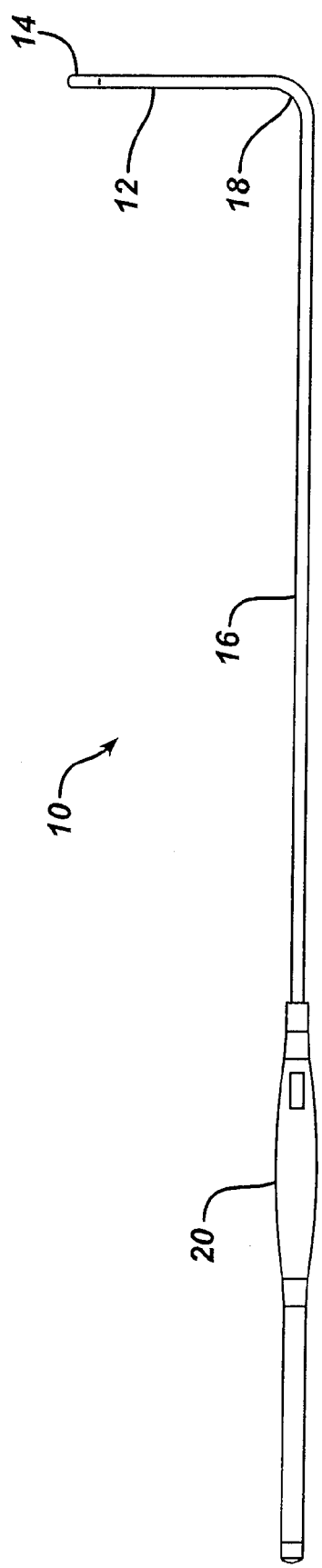
FIG. 1 a side view of a screw placement guide of the invention.
Figure 2:
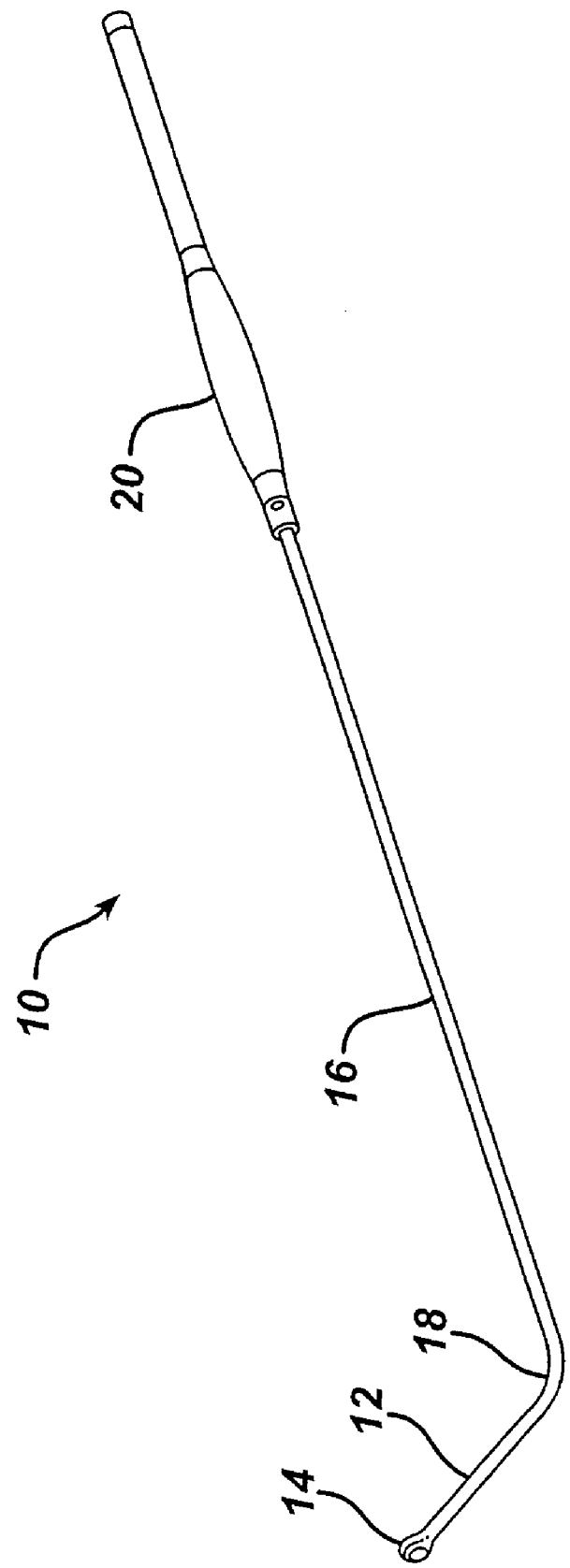
FIG. 2 is a perspective view of the screw placement guide of FIG. 1.

A screw placement guide tool 10 of the invention is illustrated in side and perspective views in FIGS. 1 and 2, respectively. Guide tool 10 includes an elongate alignment element 12 having a placement guide 14 disposed thereon. Placement guide 14 is shown as a closed loop, however, any guide or directional marker useful for placing a screw may be used. For example, placement guide 14 could simply be a blunt end against which a rod receiving screw could be aligned for placement into a patient's spine. Placement guide 14 could also provide an element for marking the bone to indicate where the screw is to be placed, or could itself be a screw holder or screw guide.

In the illustrated embodiment, guide tool 10 also includes an extension element 16 that extends substantially transversely and proximally from alignment element 12, connected to the alignment element by curved portion 18 that is designed to move through a patient without damaging nearby tissue. Extension element 16 may also include a proximal handle 20 for gripping by a surgeon. While alignment element 12 and extension member 16 are shown perpendicular to each other, a person of ordinary skill in the art will recognize that these elements could connect at any angle appropriate to the surgical procedure in which the tool is used, and that for some procedures, handle 20 and/or extension member 16 may not be required.

Figure 3:
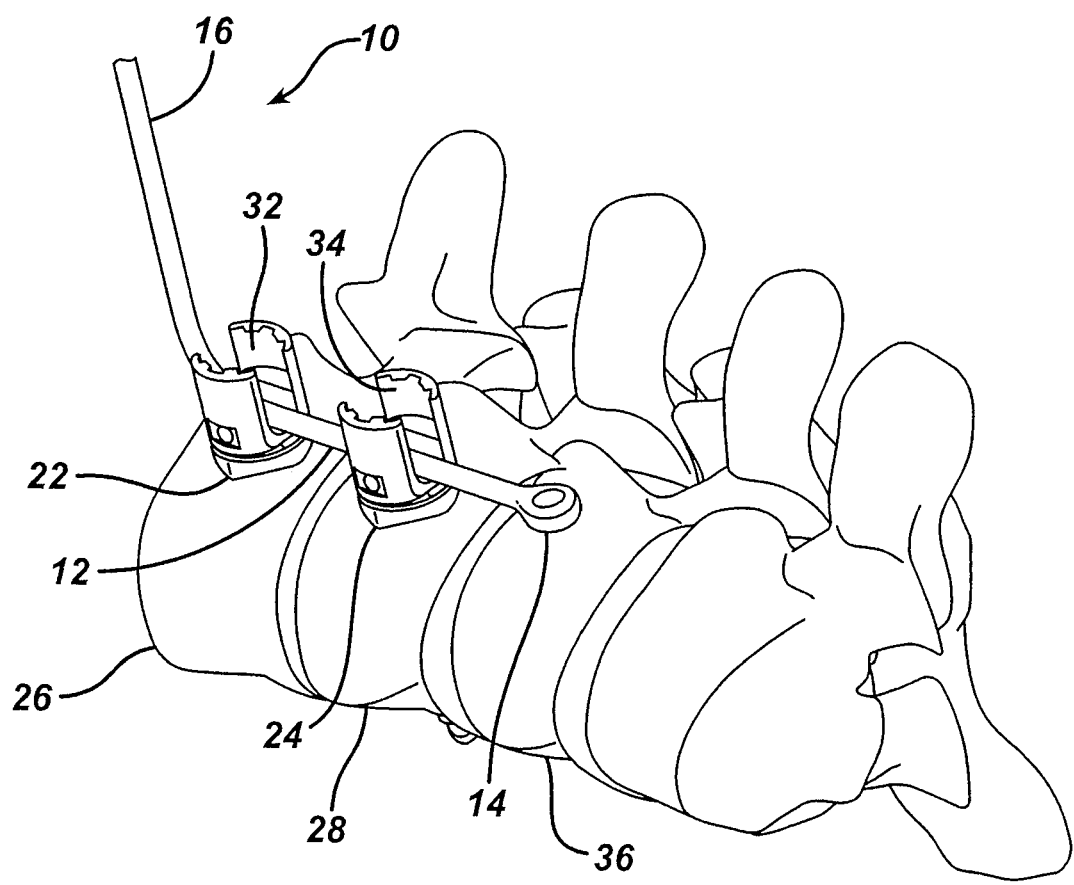
FIG. 3 illustrates the screw placement guide of FIG. 1 along with two rod receiving screws locating a placement for a third rod receiving screw on a patient's spine.

A system and method for placing a screw using screw placement guide 10 is illustrated by reference to FIGS. 3 and 4. In FIG. 3, two screws 22, 24 have been placed into vertebral bodies 26, 28, respectively, in a patient's spine 30. Each of screws 22, 24 include a bone attaching element and a "U" shaped receiving member 32, 34, respectively, connected to or integral with them. As illustrated, screw placement guide 10 has been placed so that alignment element 12 rests within each of U-shaped receiving members 32, 34 and extends over a third vertebral body 36 into which a screw will be placed.

In order to perform its intended functions, alignment element 12 will generally be sized to fit within the U-shaped receiving members, having a diameter that is substantially the same as or, more preferably, slightly smaller than the diameter of the spinal fixation rod that will be employed, often in the range of approximately 3/16 to 1/4 inches. In addition, alignment element 12 should be of a sufficient length to rest within two U-shaped receiving members and still extend to an additional screw placement site. In one preferred embodiment, alignment element 12 is about 60 millimeters in length. Alignment element 12 can also be shaped so as to have the same contour that a spinal fixation rod to be implanted will take. To that end, alignment element 12 can be contoured using the same rod template that will be used to contour the spinal fixation rod to be implanted.

Figure 4:
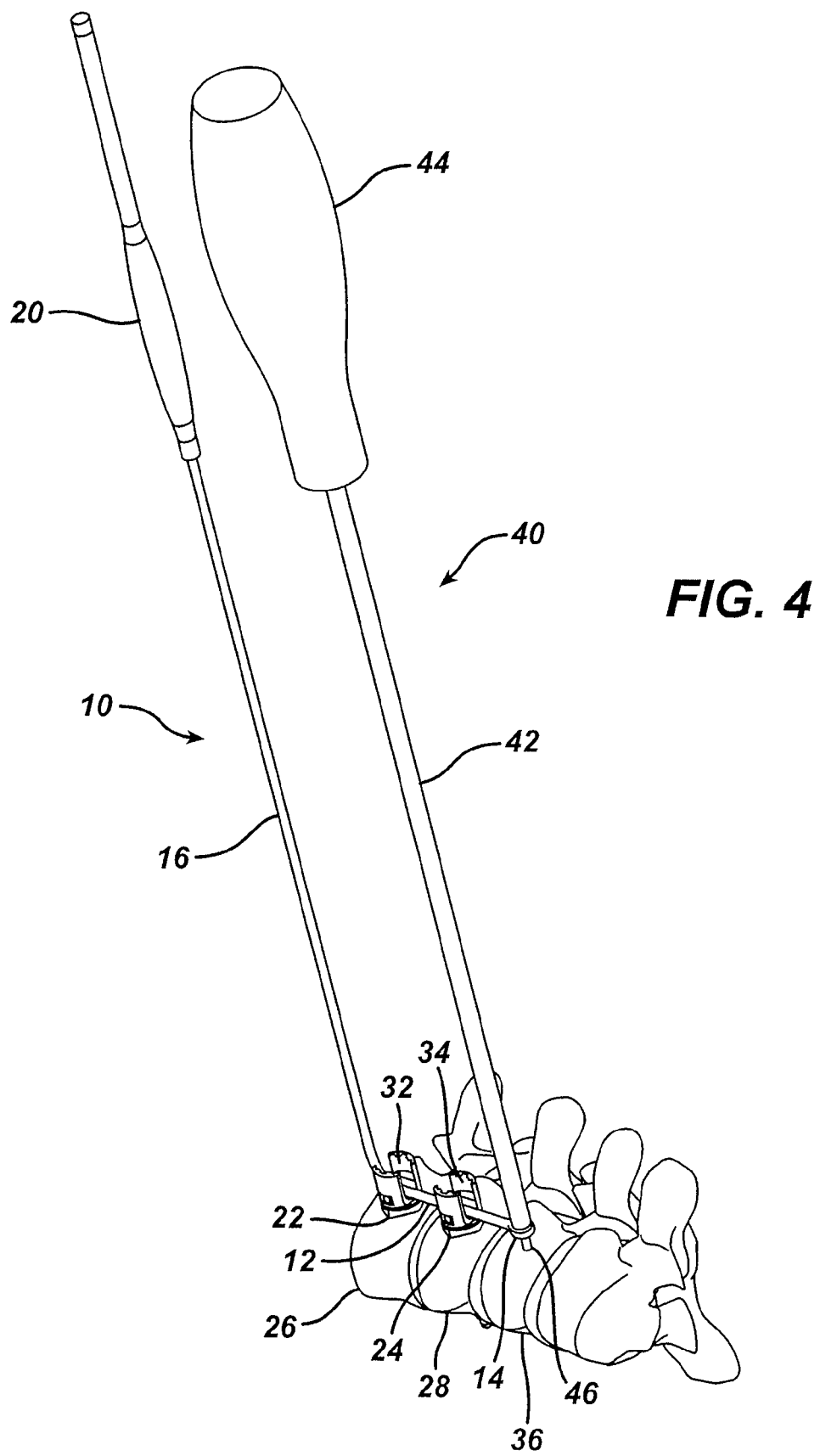
FIG. 4 illustrates the screw placement guide of FIG. 1 along with two rod receiving screws and a marking tool for marking the location for the placement of a third rod receiving screw on a patient's spine.

Turning to FIG. 4, screw placement tool 10 is illustrated having extension element 16 and proximal handle 20 as they might be configured for use in minimally invasive surgery. In this configuration, extension element 16 and handle 20 may extend approximately 200 to 400 millimeters proximally from alignment element 12 in its working position as illustrated. In this way, a surgeon can insert alignment element 12, then extension element 16 into an incision or portal being used to perform the surgery, and can operate the placement tool from outside the patient's body using handle 20.

In addition, an awl or marking tool 40 can be provided having an extension element 42 with a proximal handle 44 and a distal marking element 46 attached thereto. While in some embodiments, the screw may be placed directly in vertebral body 36 based on an indication from alignment element 12, marking tool 40 may also be used to extend through the eyelet of illustrated placement guide 14 to mark (in the illustrated case by scoring or punching a small hole) the place where a screw will be implanted. Marking tool 40 and screw placement guide 10 can then be removed and the screw may be implanted as marked on vertebral body 36. Where marking tool 40 is an awl, it can be used to start a hole that the surgeon can either tap through or insert the screw into.

While the embodiments of the invention illustrated in FIGS. 3 and 4 show screw placement tool 10 being aligned with two rod receiving screws to locate the placement of a third screw, screw placement tool 10 could readily be used with one implanted rod receiving screw to locate the placement of a second screw. To do so, a first rod receiving screw such as screw 22 is implanted. Tool 10 is then fitted so that its alignment element 12 is aligned within rod receiving opening 32 and placement guide 14 is located over vertebral body 28 to locate a desired location for implanting a second screw. The location for the second screw can then be marked and/or the screw implanted as described above.

A person of ordinary skill in the art will appreciate further features and advantages of the invention based on the above-described embodiments. For example, the invention may be applied using a variety of bone attachment devices used in spinal rod fixation including, but not limited to, each of the screws described in the Cotrel and Biedermann patents incorporated by reference above. Accordingly, the invention is not to be limited by what has been particularly shown and described, except as indicated by the appended claims. All publications and references cited herein are expressly incorporated herein by reference in their entity.

What is claimed is:

1. A method for placing a rod receiving screw for implantation in a vertebral body, comprising:
   implanting at least one rod receiving screw into a patient's spine, each of the at least one rod receiving screw having a distal bone attachment element and a proximal rod receiving opening;
   fitting a screw placement guide tool having an elongate alignment element including a screw placement guide located thereon within the rod receiving opening of the at least one implanted rod receiving screw so that the screw placement guide indicates a placement location for another rod receiving screw; and
   implanting another rod receiving screw at the placement location.

2. The method of claim 1, wherein at least two rod receiving screws are implanted into a patient's spine and the screw placement guide tool is fitted to the rod receiving openings of the at least two implanted rod receiving screws so that the placement guide indicates a placement location for a third rod receiving screw.

3. The method of claim 1, wherein the screw placement guide tool further includes an extension member extending proximally from the alignment element and a handle disposed on a proximal portion of the alignment element so that a surgeon may operate the tool using the handle portion external to a patient's body to fit the alignment element within the rod receiving openings of the at least two implanted rod receiving screws.

4. The method of claim 1, further comprising curving the alignment element to correspond to a curve of a spinal fixation rod to be implanted.

5. The method of claim 1, wherein the alignment element has first and second opposed ends, is connected to the extension member at a first opposed end, and has the screw placement guide located on the second opposed end.

6. The method of claim 1, further comprising:
   guiding a marking tool to a location indicated by the screw placement guide; and
   placing an indication on a patient's bone where a screw is to be implanted using the marking tool.

7. A method for placing a rod receiving screw for implantation in a vertebral body, comprising:
   implanting a first rod receiving screw into a first vertebra, the first rod receiving screw having a distal bone attachment element and a proximal rod receiving opening;
   providing a screw placement guide tool having an elongate alignment element;
   operating the screw placement guide tool to place the elongate element within the rod receiving opening of the first rod receiving screw so that the elongate element indicates a placement location for a second rod receiving screw on a second vertebra;
   implanting the second rod receiving screw, the second rod receiving screw having a distal bone attachment element and a proximal rod receiving opening, in the second vertebra at the placement location indicated by the screw placement guide tool.

8. The method of claim 7, further comprising implanting a third rod receiving screw into a third vertebra, the third rod receiving screw having a distal bone attachment element and a proximal rod receiving opening, and wherein the step of operating the screw placement guide tool includes placing the elongate element within the rod receiving openings of the first and third rod receiving screws.

9. The method of claim 7, wherein the alignment element is curved to correspond to a curve of a spinal fixation rod to be implanted.

10. The method of claim 7, wherein the elongate alignment element has a screw placement guide located thereon.

11. The method of claim 10, wherein the screw placement guide is a loop.

12. The method of claim 10, wherein the screw placement guide is has a blunt end.

13. The method of claim 7, wherein the alignment element has first and second opposed ends, is connected to the extension member at a first opposed end, and has the screw placement guide located on the second opposed end.

14. The method of claim 7, further comprising providing a marking tool, and operating the marking tool to place an indication on a patient's bone at the location indicated by the screw placement guide.

15. The method of claim 7, wherein the screw placement guide tool includes an extension member provided at an angle to the elongate alignment element and having a handle disposed on a proximal portion of the extension member.

16. The method of claim 15, further comprising operating the handle from a location outside of the patient's body to place the alignment element within the rod receiving opening of the at least one implanted rod receiving screw so that the screw placement guide indicates a placement location for another rod receiving screw.

17. A method for placing a rod receiving screw for implantation in a vertebral body, comprising:

implanting a first rod receiving screw into a first vertebra, the first rod receiving screw having a distal bone attachment element and a proximal rod receiving opening;

providing a screw placement guide tool having an elongate alignment element including a screw placement guide located thereon;

operating the screw placement guide tool to place the elongate element within the rod receiving opening of the first rod receiving screw so that the screw placement guide indicates a placement location for a second rod receiving screw on a second vertebra;

implanting the second rod receiving screw in the second vertebra at the placement location indicated by the screw placement guide.

18. The method of claim 17, further comprising implanting a third rod receiving screw into a third vertebra, the third rod receiving screw having a distal bone attachment element and a proximal rod receiving opening, and wherein the step of operating the screw placement guide tool includes placing the elongate element within the rod receiving openings of the first and third rod receiving screws.

19. The method of claim 17, wherein the alignment element is curved to correspond to a curve of a spinal fixation rod to be implanted.

20. The method of claim 17, wherein the screw placement guide is a loop.

21. The method of claim 17, wherein the alignment element has first and second opposed ends, is connected to the extension member at a first opposed end, and has the screw placement guide located on the second opposed end.

22. The method of claim 17, further comprising providing a marking tool, and operating the marking tool to place an indication on a patient's bone at the location indicated by the screw placement guide.

23. The method of claim 17, wherein the screw placement guide tool includes an extension member provided at an angle to the elongate alignment element and having a handle disposed on a proximal portion of the extension member.

24. The method of claim 23, further comprising operating the handle from a location outside of the patient's body to place the alignment element within the rod receiving opening of the first rod receiving screw so that the screw placement guide indicates a placement location for another rod receiving screw.

25. The method of claim 24, further comprising providing a marking tool, and operating the marking tool to place an indication on a patient's bone at the location indicated by the screw placement guide.

26. The method of claim 24, wherein the screw placement guide tool is removed before implanting a rod receiving screw at the placement location indicated.

27. The method of claim 24, wherein the alignment element is curved to correspond to a curve of a spinal fixation rod to be implanted.

28. The method of claim 24, wherein the screw placement guide is a loop.

29. The method of claim 24, wherein the alignment element has first and second opposed ends, is connected to the extension member at a first opposed end, and has the screw placement guide located on the second opposed end.

30. The method of claim 24, wherein the screw placement guide tool includes an extension member provided at an angle to the elongate alignment element and having a handle disposed on a proximal portion of the extension member.

31. The method of claim 30, further comprising operating the handle from a location outside of the patient's body to place the alignment element within the rod receiving opening of the implanted first rod receiving screw so that the screw placement guide indicates a placement location for another rod receiving screw.

* * * * *

UNITED STATES PATENT AND TRADEMARK OFFICE
CERTIFICATE OF CORRECTION

| | | |
|---|---|---|
| PATENT NO. | : 7,981,117 B2 | Page 1 of 1 |
| APPLICATION NO. | : 11/946382 | |
| DATED | : July 19, 2011 | |
| INVENTOR(S) | : Peter Newton et al. | |

It is certified that error appears in the above-identified patent and that said Letters Patent is hereby corrected as shown below:

In the claims:

At column 6, line 47, in claim 12, change

"guide is has a blunt end."

to

"guide has a blunt end."

Signed and Sealed this
Twenty-seventh Day of September, 2011

David J. Kappos
*Director of the United States Patent and Trademark Office*